US007981125B1

United States Patent
Colvin et al.

(10) Patent No.: US 7,981,125 B1
(45) Date of Patent: Jul. 19, 2011

(54) SURGICAL KNOT PUSHER AND CUTTER (75) Inventors: Stephen B. Colvin, New York, NY (US); Allan Katz, Freeport, NY (US); Eugene A. Grossi, New York, NY (US); Aubrey C. Galloway, Jr., Bronxville, NY (US)

(73) Assignee: Endoscopic Technologies, Inc., San Ramon, CA (US)

( * ) Notice: Subject to any disclaimer, the term of this patent is extended or adjusted under 35 U.S.C. 154(b) by 486 days.

(21) Appl. No.: 11/112,977

(22) Filed: Apr. 22, 2005

Related U.S. Application Data (60) Provisional application No. 60/623,288, filed on Oct. 29, 2004.

(51) Int. Cl.
*A61B 17/04* (2006.01)
(52) U.S. Cl. .................................................. 606/148
(58) Field of Classification Search .............. 606/139, 606/144–148, 167, 170; 30/152, 162, 124, 30/62, 127, 351; 112/80.03, 169, 136; 289/17, 289/1.2, 1.5, 18.1, 2, 15
See application file for complete search history.

(56) References Cited

U.S. PATENT DOCUMENTS

| | | | | |
|---|---|---|---|---|
| 1,625,602 A * | 4/1927 | Gould et al. | .................. | 606/139 |
| 4,188,052 A * | 2/1980 | Browning | .................. | 289/17 |
| 4,403,797 A * | 9/1983 | Ragland, Jr. | .................. | 289/17 |
| 4,961,741 A * | 10/1990 | Hayhurst | .................. | 606/139 |
| 5,133,723 A * | 7/1992 | Li et al. | .................. | 606/148 |
| 5,176,691 A * | 1/1993 | Pierce | .................. | 606/148 |
| 5,423,837 A * | 6/1995 | Mericle et al. | .................. | 606/148 |
| 5,439,470 A * | 8/1995 | Li | .................. | 606/148 |
| 5,752,964 A * | 5/1998 | Mericle | .................. | 606/148 |
| 5,759,189 A * | 6/1998 | Ferragamo et al. | .................. | 606/148 |
| 5,797,928 A * | 8/1998 | Kogasaka | .................. | 606/144 |
| 5,797,929 A * | 8/1998 | Andreas et al. | .................. | 606/148 |
| 5,860,993 A * | 1/1999 | Thompson et al. | .................. | 606/148 |
| 2002/0123758 A1* | 9/2002 | Bachman et al. | .................. | 606/148 |
| 2003/0109891 A1* | 6/2003 | Dana et al. | .................. | 606/148 |

* cited by examiner

*Primary Examiner* — Darwin P Erezo
*Assistant Examiner* — Dianne Dornbusch
(74) *Attorney, Agent, or Firm* — Sterne, Kessler, Goldstein & Fox P.L.L.C.

(57) ABSTRACT

A solution is provided to push a knot and/or cut a suture using a housing having a tip, a first side and a second side, the first side and the second side having a recessed center. The housing further has at least one slit positioned at the tip, and a blade moveable between retracted and extended positions, and positioned within the housing such that the blade passes through the slit as it is moved from the retracted position to the extended position within the slit. A notch may be positioned at the tip to push the knot to a desired position.

7 Claims, 7 Drawing Sheets

SURGICAL KNOT PUSHER AND CUTTER

CROSS-REFERENCE TO RELATED APPLICATION

This application claims priority based on U.S. Patent Provisional Application Ser. No. 60/623,288, entitled "Surgical Knot Pusher And Cutter" by Stephen B. Colvin, Alan Katz, Dr. Eugene Grossi and Aubrey C. Galloway, filed on Oct. 29, 2004.

FIELD OF THE INVENTION

The present invention relates to medical devices. More particularly, the present invention relates to medical devices for securing sutures and cutting the suture ends.

BACKGROUND OF THE INVENTION

The majority of surgical procedures rely upon various types of sutures for not only closing incisions, but also for connecting and/or supporting structures within the body. The use of sutures also usually requires the tying of one or more knots in order to secure the suture in place. There are many ways for tying sutures and will not be discussed here in detail to prevent obfuscation of the present invention. However, for exemplary purposes only, one known procedure is a "taut-line hitch" knot. The knot is formed in the loose ends of the suture at a location remote from the surgical site from which the suture ends emanate, and then the knot is run down the suture ends to the surgical site by pulling with a sawing motion on the appropriate suture ends. A significant drawback to this procedure is that as the appropriate suture end is pulled through the tissue in which the suture is implanted so as to run the knot down to the surgical site, the sawing motion imparted to the suture ends causes the latter to tend to cut and abrade the tissue.

An alternative procedure consists of forming a throw in the suture at a location remote from the surgical site from which the suture ends emanate, running the throw down the length of suture to the surgical site, forming a second throw in the suture at a location remote from the surgical site, running that throw down the length of suture to the surgical site so that it sits atop the first throw, and thereafter repeating the foregoing process as many times as necessary so as to form the desired knot at the surgical site. As used herein, a "turn" consists of two ends of suture which are looped over one another one or more times, a "throw" consists of one or more turns, and a "knot" consists of two or more throws laid on top of one another and tightened so as to lock the two strands of suture relative to one another.

After the knot is tied, the pair of suture tails extending from the knot normally must be cut. If the tails are cut too short or unevenly, the knot may become untied. Alternatively, if the tails are left too long, the suture tails may be irritating to the patient or become entangled with other structures. The term "suture tail" is meant to include any length of suture, whether or not it is extending from a knot.

The cutting of suture tails can often be accomplished merely by employing surgical scissors, particularly when the knot is located outside of the patient's body. Many times, however, the knot and accompanying suture tails are located within the patient's body, or within an orifice of the patient's body. For example, sutures may be tied within the abdomen or heart of a patient during a surgical procedure. In these instances, it may be difficult for medical personnel to safely employ standard surgical scissors to cut the sutures after tying. Thus, various types of suture-cutting devices have been developed which enable the medical personnel to cut the sutures in a location which normally would not be accessible to a pair of conventional scissors. These devices of the prior art suffer from many drawbacks, however, including the risk of the cutting blade inadvertently injuring the patient or physician or cutting the tissue or a blood vessel. In addition, vision is often impaired during these procedures, and thus it can be difficult for the medical personnel to insure that the suture tails are left at the proper length. Most of these devices are also unable to simultaneously cut both tails. Thus, a reliable suture cutting device is needed whereby a surgeon can rapidly and accurately trim back the strands from a knot.

BRIEF DESCRIPTION OF THE INVENTION

A solution is provided to push a knot and/or cut a suture using a housing having a tip, a first side and a second side, the first side and the second side having a recessed center. The housing further has at least one slit positioned at the tip, and a blade moveable between retracted and extended positions, and positioned within the housing such that the blade passes through the slit as it is moved from the retracted position to the extended position within the slit. A notch may be positioned at the tip to push the knot to a desired position.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings.

DETAILED DESCRIPTION

Embodiments of the present invention are described herein in the context of a surgical knot pusher and cutter. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1A:
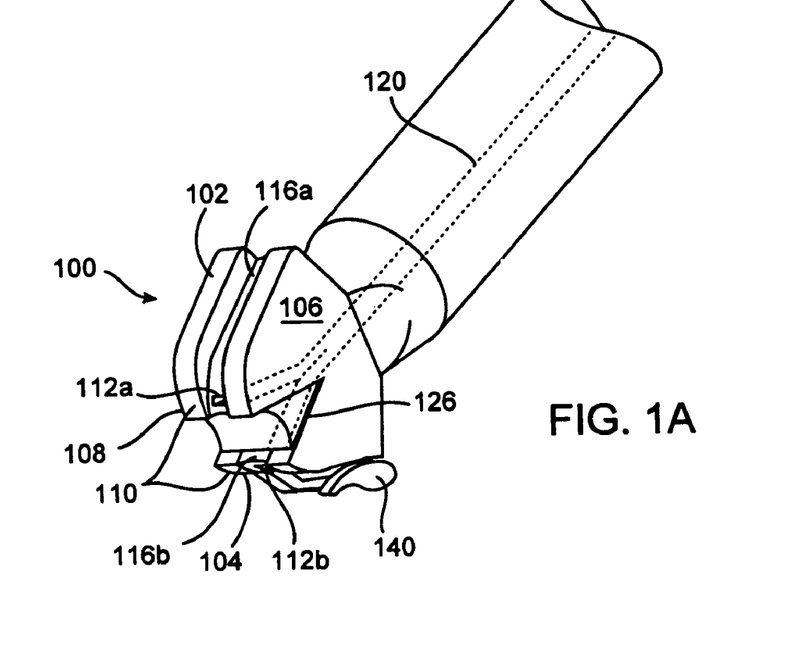
FIGS. 1A, 1B, and 1C illustrate the surgical knot pusher and cutter housing in accordance with an embodiment of the present invention.
Figure 1B:
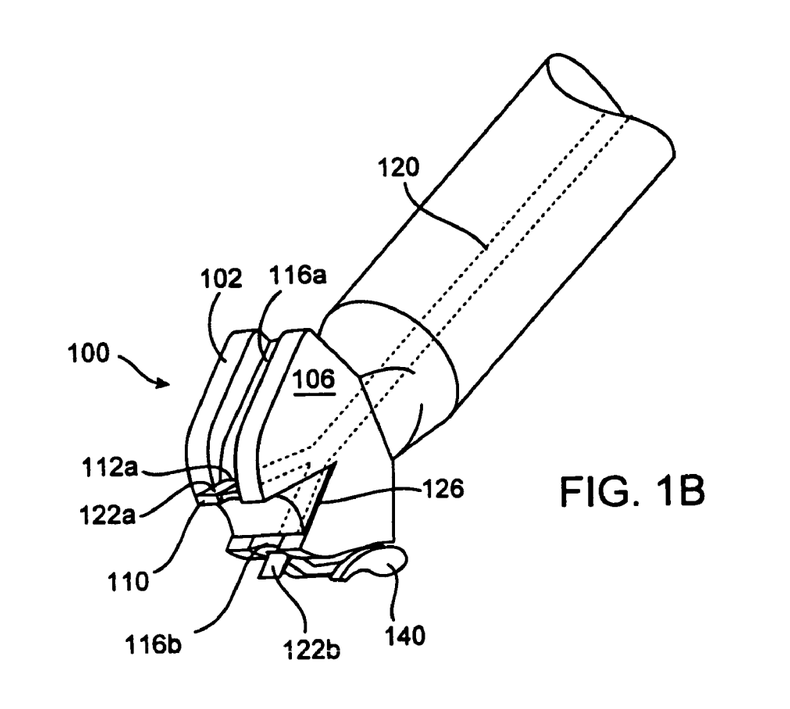
Figure 1C:
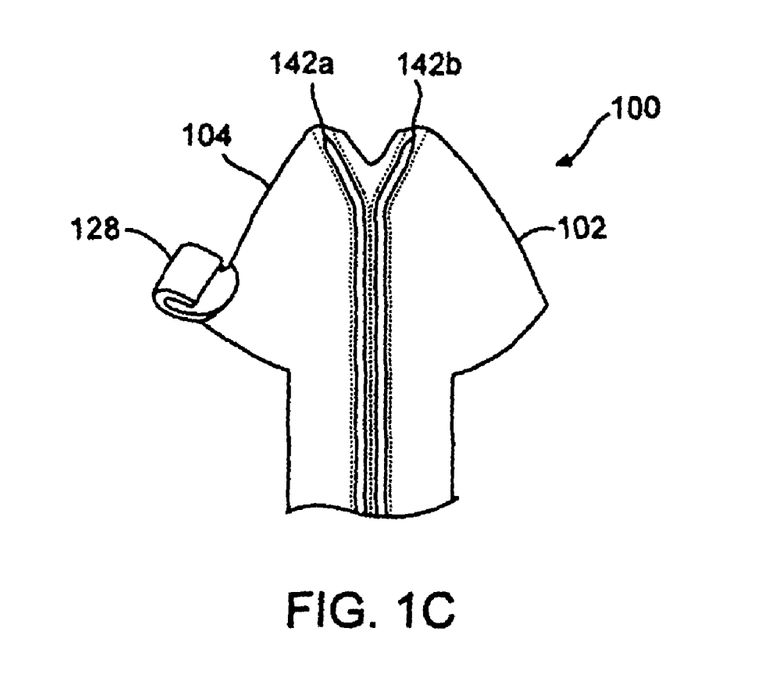
Figure 2A:
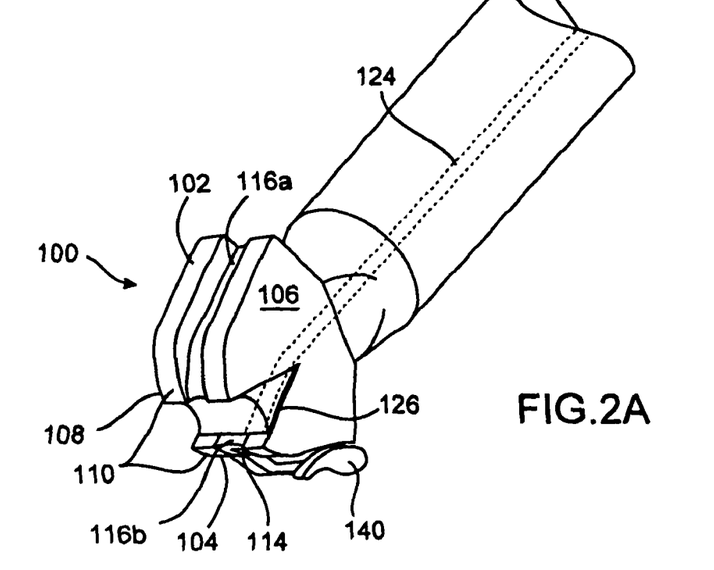
FIGS. 2A, 2B, and 2C illustrate the surgical knot pusher and cutter housing in accordance with another embodiment of the present invention.
Figure 2B:
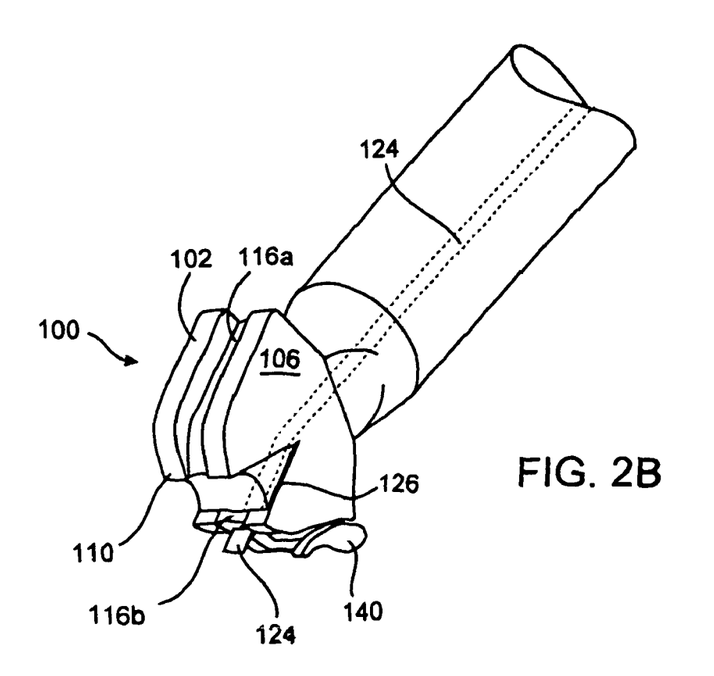
Figure 2C:
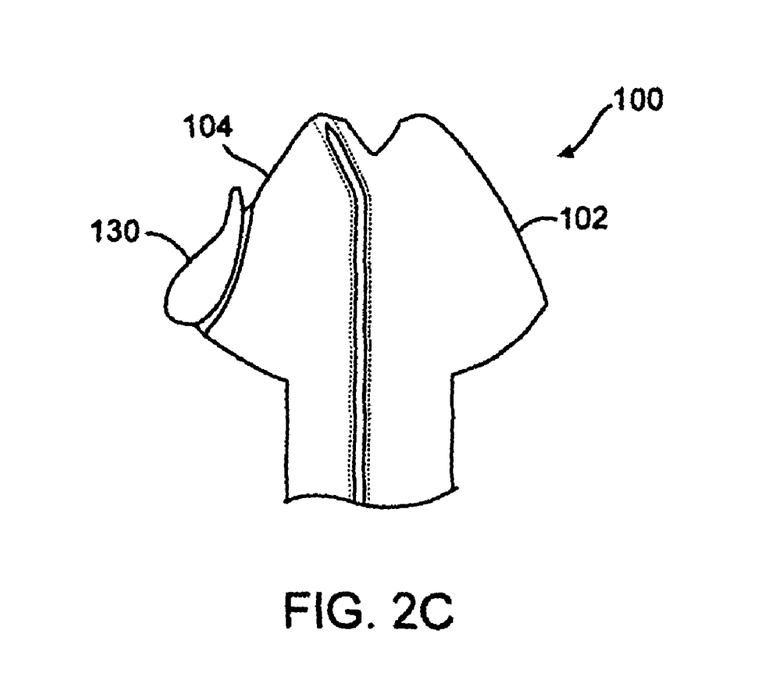

The present invention provides for a reliable suture cutting device whereby a surgeon can rapidly and accurately trim back the strands from a knot in a location that is not visible or difficult to reach by hand. FIGS. 1A-1C illustrate the surgical knot pusher and cutter housing in accordance with an embodiment of the present invention. FIGS. 2A-2C illustrate the surgical knot pusher and cutter housing in accordance with another embodiment of the present invention. Referring now to FIGS. 1A and 2A, the device has a housing 100 which may be made of any biocompatible material such as light weight, molded plastic, metal, and the like. The housing may have a first side 102, a second side 104, a top surface 106, a bottom surface 108, and a tip 110. The tip 110, being blunt to prevent damage to the patient, may have at least one slit 112a and 112b. As illustrated in FIG. 2A, the tip may have a single slit 114 positioned at the tip 110.

The first side 102 and second side 104 each have a recessed center 116a, 116b. The recessed center allows for the suture to be positioned adjacent the housing 100 as the knot is pushed toward the desired location as will be discussed in further detail below.

A blade may be positioned within the housing such that it is movable between a retracted and extended position. The blade may be made of a strong, but resilient biocompatible material such as steel, and the like. FIGS. 1A and 2A illustrate the blade in a retracted position and not exposed, thereby eliminating the possibility of injury to the patient or user. However, FIGS. 1B and 2B illustrate the blade in an extended position. As illustrated in FIG. 1B, the blade may have a first prong 122a and a second prong 122b positioned in a V shape. The blade 120 may be positioned within the housing 100 such that it passes through the slits 112a, 112b in the extended position. As illustrated in FIG. 2B, the blade 124 may only have a single prong 126 angled toward the suture guide member 140. The blade 124 is positioned within the housing 100 such that it passes through the single slit 114 in the extended position. Alternatively, the blade may be two separate blades 142a, 142b as illustrated in FIG. 1C.

The housing 100 may also have a recessed notch 126 at the tip 110 that extends between the top surface 106 and the bottom surface 108. The notch 126 may be used to push the knot to the desired position as will be discussed in further detail below. The notch 126 may be shaped as a triangle as illustrated or any other shape that is able to push the knot. The recessed center 116a, 116b and recessed notch 126 allows the user to securely position the suture adjacent the housing 100 as the knot is pushed to the desired location.

The housing 100 may also have at least one suture guide member. As illustrated in FIG. 1C, a top view of the housing 100, the suture guide member 128 may comprise an open encasement to easily position the suture(s) into. As illustrated in FIG. 2C, the suture guide member 130 may comprise a snap fit encasement to secure the suture adjacent the housing 100 such that the user may be required to use slight force to insert the suture into the suture guide member 130. As opposed to guide member 128, in this embodiment, the suture could not freely release from the guide member 130. The suture guide members 128, 130 are illustrated with various shapes, however, the shapes are not intended to be limiting as any shape may be used to secure the suture adjacent the housing 100. Additionally, the suture guide 128, 130 may be positioned either on the first 102 or second 104 side of the housing 100. Furthermore, although illustrated with the use of a single suture guide member 128, 130, the number is not intended to be limiting as a number of suture guide members may be used such as a suture guide member on each side of the housing.

Figure 3A:
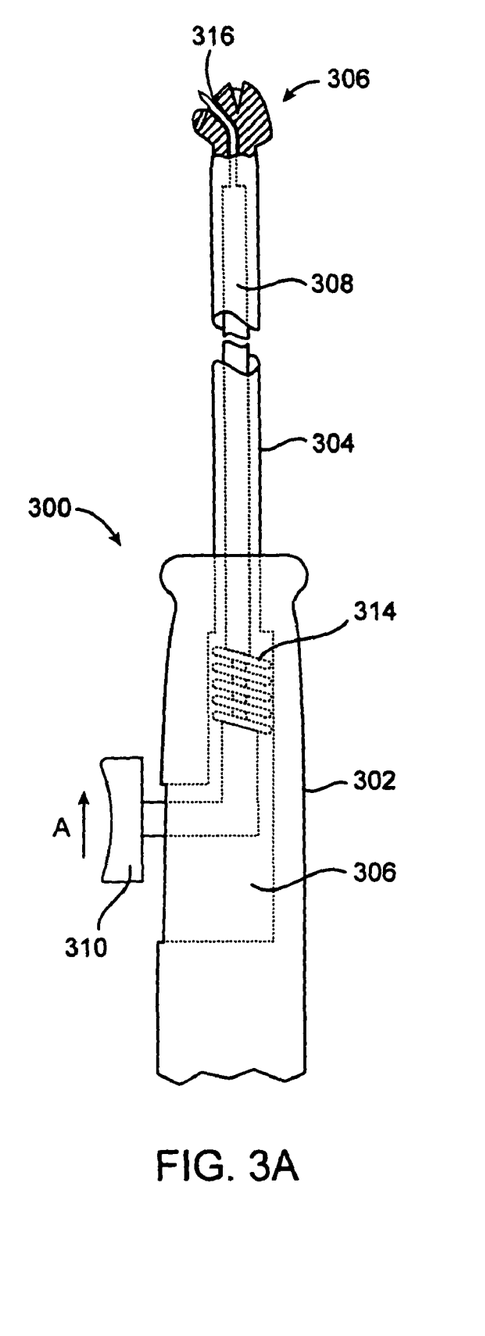
FIGS. 3A and 3B illustrate the surgical knot pusher and cutter in accordance with an embodiment of the present invention.
Figure 3B:
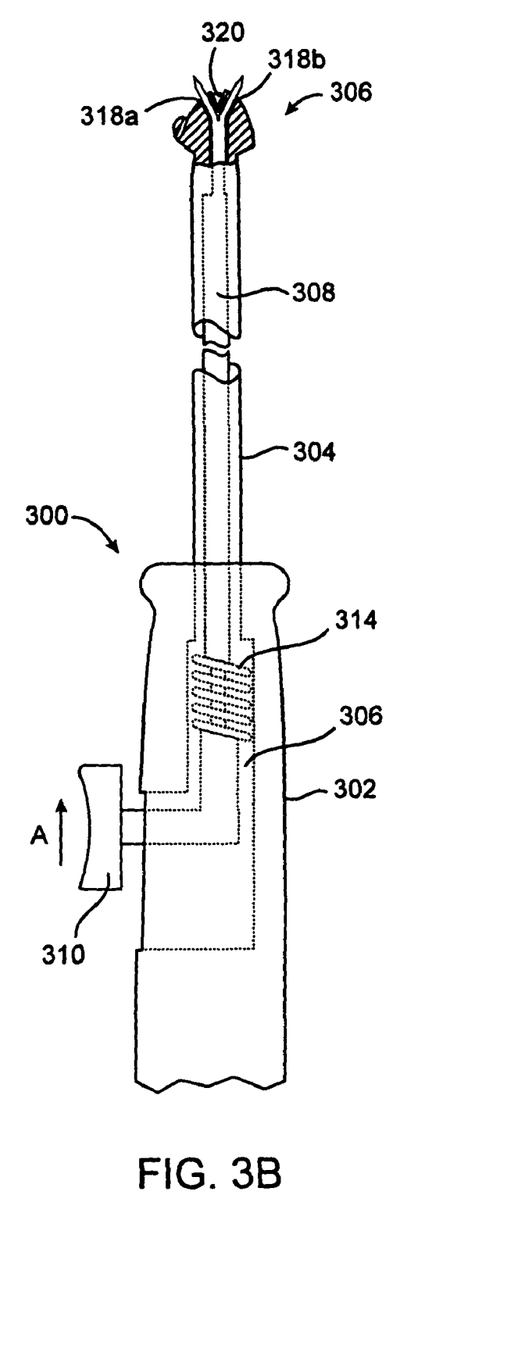

FIGS. 3A and 3B illustrate the surgical knot pusher and cutter in accordance with an embodiment of the present invention. The device, generally numbered 300 may have a handle 302 having an elongated shaft 304 and a lumen 306 extending from the handle 302 to the shaft 304. The housing 306 may be connected to the opposite end of the shaft 304. The housing 306 may be the housing illustrated in FIG. 1A or 2A. The handle 302 may be configured so as to be easily grasped and manipulated by a user during use.

A blade 308 may be positioned within the lumen 306 and may be moveable between a retracted and extended position within the lumen 306. The blade 308 may be in communication with a blade pusher 310 through a spring member 314. The blade pusher 310 may extend out of an opening 312 in the handle 302. Although the blade pusher 310 is illustrated as extending outwardly from the handle 302, the blade pusher 310 may also be designed to be flush with the handle 302. When the blade pusher 310 is pushed in the direction of arrow A, the spring 314 is compressed, which causes the blade 308 to also move in the direction of arrow A. The blade 308 may then exit through slits 316 (318a, 318b in FIG. 3B) and be in its extended position to cut the suture strands adjacent the knot.

As illustrated in FIG. 3B, the notch 320 may be used to prevent blade 308 from extending too far outwardly to thereby prevent damage to the surrounding tissue or blood vessel.

Figure 4A:
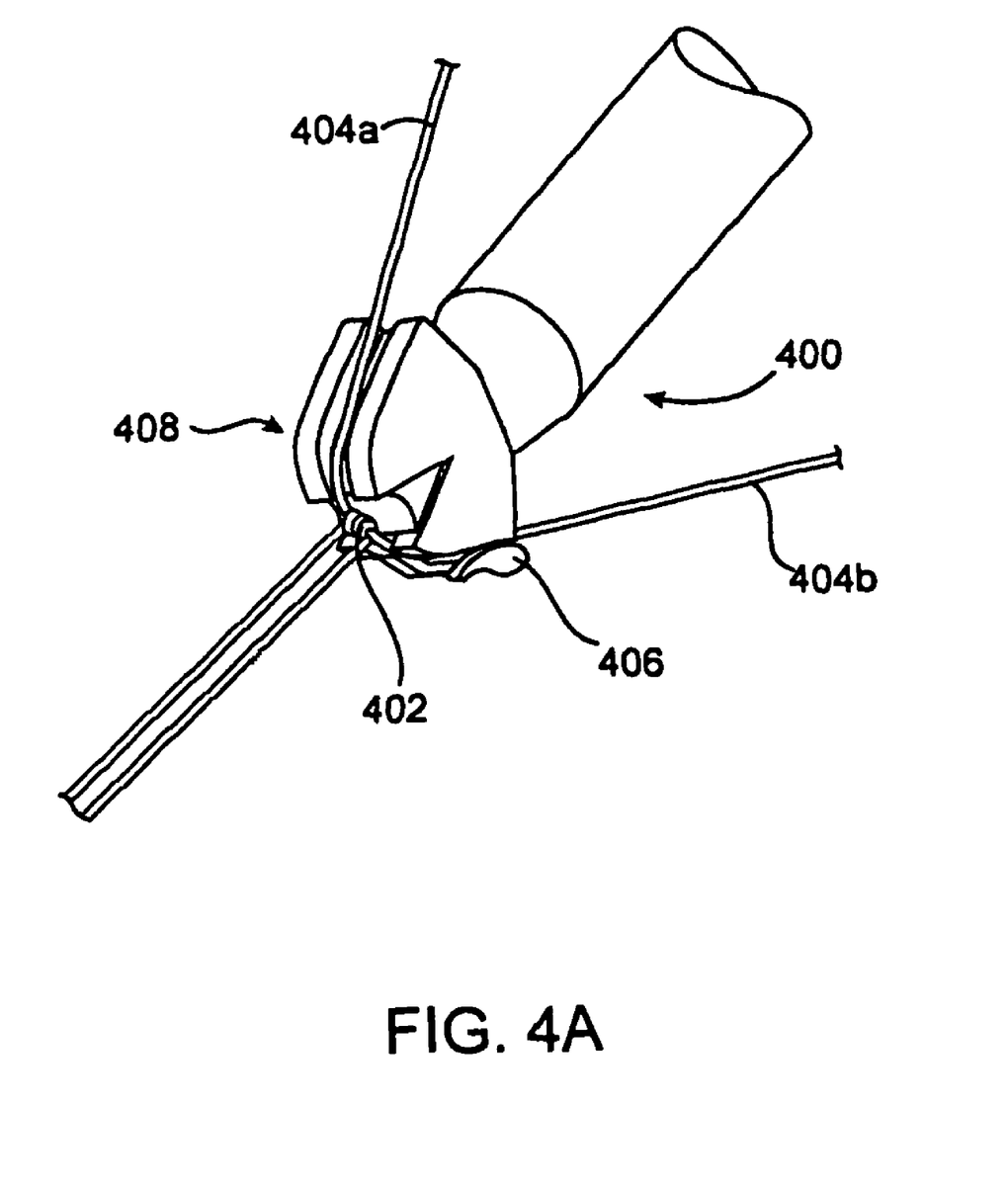
FIGS. 4A, 4B, and 4C illustrate the use of the surgical knot pusher and cutter device in accordance with an embodiment of the present invention.
Figure 4B:
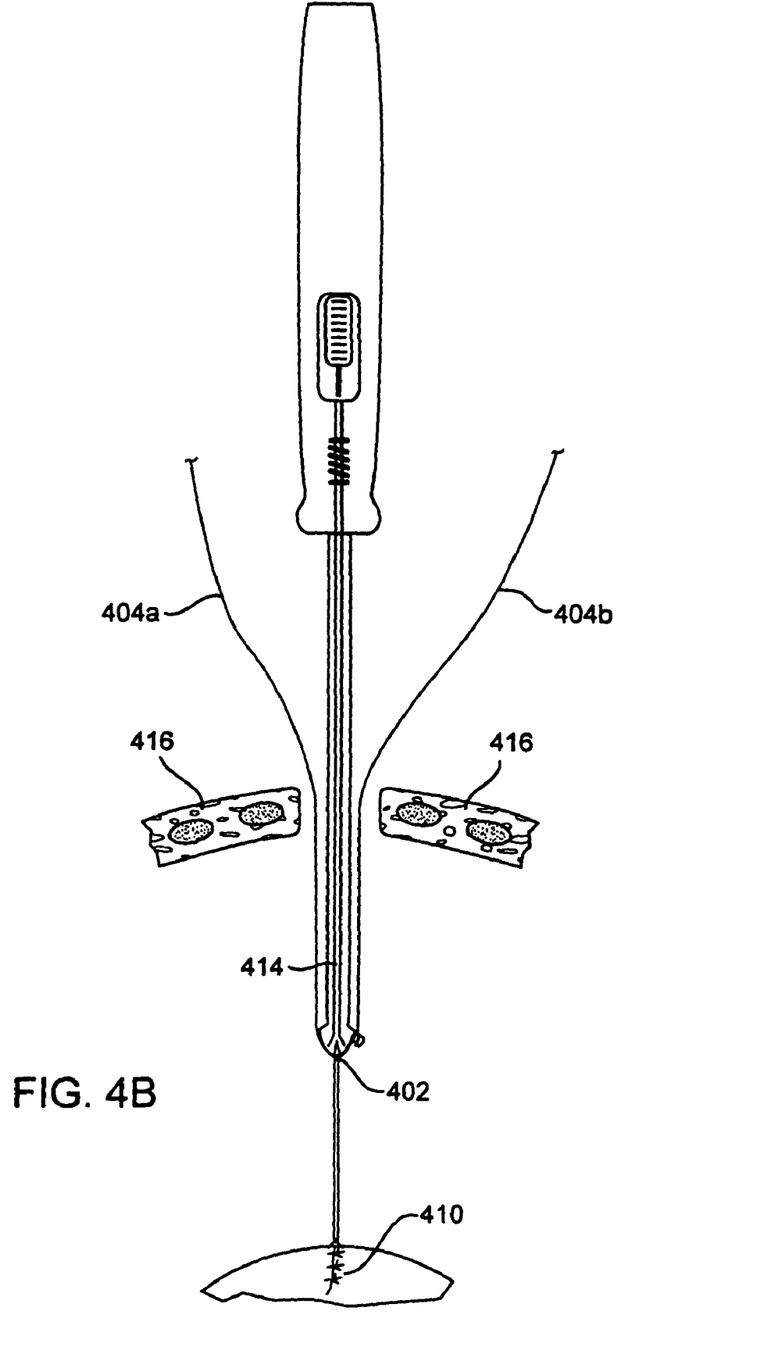
Figure 4C:
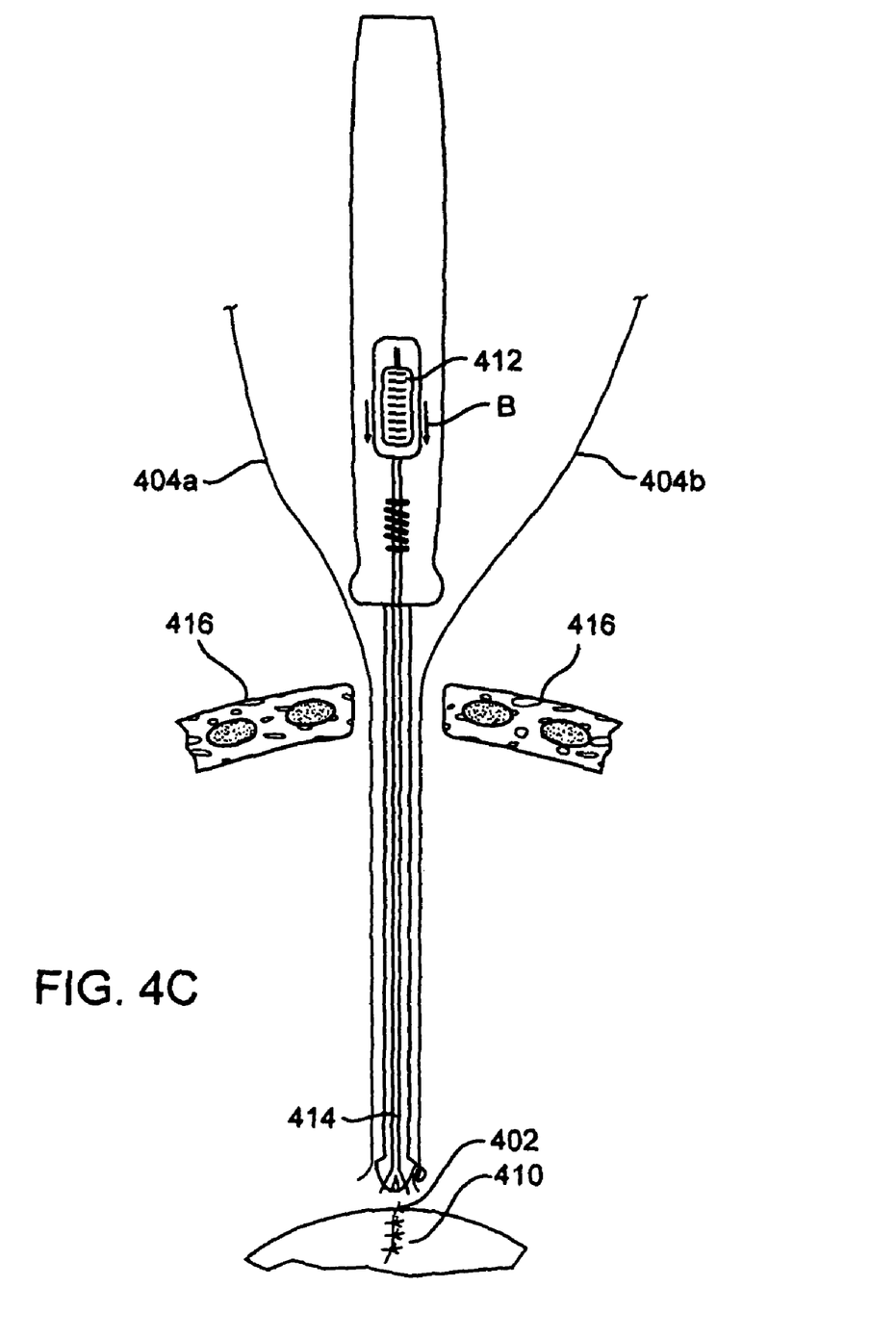

FIGS. 4A, 4B, and 4C illustrate the use of the surgical knot pusher and cutter device in accordance with an embodiment of the present invention. The pushing and cutting of a knot may be possible with the use of one hand and one instrument. As illustrated in FIG. 4A, once a knot 402 is formed external the patient's body, by any known means as described above, the device 400 may be positioned above the knot 402 such that the knot 402 and sutures 404a, 404b are positioned within the recessed areas of the housing 408. The suture 404b may also be positioned within the suture guide member 406 to further guide the user to the desired position and to secure the suture adjacent the housing 408.

Once positioned in the housing 408, the knot 402 may be pushed toward the closure site 410. The blade 414 is in the retracted position as the device is pushed below the skin surface 416. Once at the closure site 410, the sutures 404a, 404b may be cut by moving blade pusher 412 in the direction of arrow B as illustrated in FIG. 4C. Blade 414 will extend out of the slits and cut the sutures 404a, 404b adjacent the knot 402. This ensures that the sutures 404a, 404b are cut adjacent the knot 402 such that the tail is long enough to sure that the knot 402 will not come undone, yet not too long to cause any irritation to the patient. Furthermore, the device may be used to push and cut knots in positions which are difficult to see and/or reach.

The procedure to push the knot and cut the suture may be performed with one instrument and one hand allowing for more flexibility to a surgeon to perform other tasks. Additionally, the embodiments allow for additional flexibility for a surgeon to cut either one suture or two sutures on one side with a single pronged blade or the surgeon may cut two sutures at opposing sides with a two-pronged blade.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. An apparatus to push a knot and/or cut a suture, comprising:
    a proximal handle;
    a shaft extending distally from the proximal handle;
    a housing extending distally from the shaft and having a tip, a first side and a second side, said first side and said second side having a recessed center;
    a first blade moveable between retracted and extended positions, and positioned within said housing such that an end of the first blade passes through a first slit and out of the housing as the first blade is moved from the retracted position to the extended position, wherein the first blade is angled toward the first side of the housing;
    a second blade moveable between retracted and extended positions and moveable relative to the first blade, and positioned within said housing such that an end of the second blade passes through a second slit and out of the housing as the second blade is moved from the retracted position to the extended position, wherein the second blade is angled toward the second side of the housing; and
    a suture guide coupled to and extending from the first side of the housing to secure the suture adjacent to the housing.

2. The apparatus of claim 1 further comprising a notch positioned at the tip to push the knot to a desired position.

3. The apparatus of claim 2 wherein said notch is a triangular shape.

4. The apparatus of claim 1 further comprising a second suture guide coupled to and extending from the second side of the housing.

5. The apparatus of claim 1, wherein the suture guide comprises an open encasement.

6. The apparatus of claim 1, wherein the suture guide comprises a snap fit encasement to secure the suture to the housing.

7. The apparatus of claim 1 further comprising:
    a lumen extending through the handle and the shaft; and
    a blade pusher coupled to the handle and in communication with at least one of the first and 2nd blades.

* * * * *